US00PP23377P2

(12) United States Plant Patent
Ferguson et al.

(10) Patent No.: US PP23,377 P2
(45) Date of Patent: Feb. 5, 2013

(54) STRAWBERRY PLANT NAMED 'DRISSTRAWTWENTYSIX'

(50) Latin Name: *Fragaria×ananassa*
Varietal Denomination: DrisStrawTwentySix

(75) Inventors: Michael D. Ferguson, Moorpark, CA (US); Terrance C. Moran, Ojai, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 13/317,067

(22) Filed: Oct. 7, 2011

(51) Int. Cl.
*A01H 5/00* (2006.01)

(52) U.S. Cl. ..... Plt./208

(58) Field of Classification Search ..... Plt./208
See application file for complete search history.

*Primary Examiner* — Annette Para
(74) *Attorney, Agent, or Firm* — Jondle & Associates, P.C.

(57) ABSTRACT

A new and distinct variety of strawberry plant named 'DrisStrawTwentySix' characterized by having large, conical fruit with medium sweetness and high yield is disclosed.

3 Drawing Sheets

Genus and species: *Fragaria×ananassa.*
Variety denomination: 'DrisStrawTwentySix'.

BACKGROUND OF THE NEW PLANT

The present invention relates to a new and distinct strawberry variety designated 'DrisStrawTwentySix' and botanically known as *Fragaria×ananassa*. This new strawberry variety was discovered in Ventura County, Calif. in January 2007 and originated from a cross between the proprietary female parent '18L33' (unpatented) and the proprietary male parent '193M68' (unpatented). A single plant was selected for asexual propagation via tissue culture and vegetative cuttings in Shasta County, Calif. in 2007.

'DrisStrawTwentySix' underwent further testing in Ventura County, Calif. for five years (2007-2011). The present invention has been found to retain its distinctive characteristics through successive asexual propagations via stolons.

Plant Breeder's Rights for this variety have not been applied for. 'DrisStrawTwentySix' has not been made publicly available or sold more than one year prior to the filing date of this application.

SUMMARY OF THE INVENTION

The following are the most outstanding and distinguishing characteristics of this new cultivar when grown under normal horticultural practices in Ventura County, Calif.

1. High yield;
2. Large, conic shaped fruit; and
3. Very early harvest maturity.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from six-month-old plants.

DESCRIPTION OF THE NEW VARIETY

Figure 1:
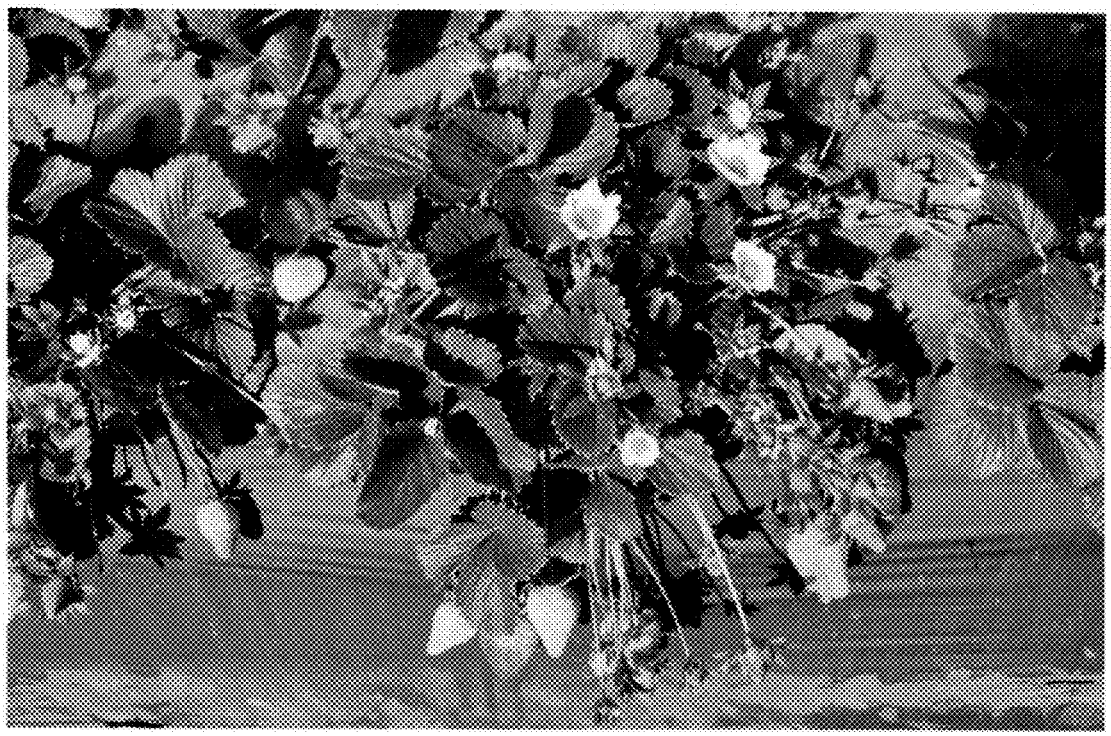
FIG. 1 shows overall plant habit including fruit at various stages of development.
Figure 2:
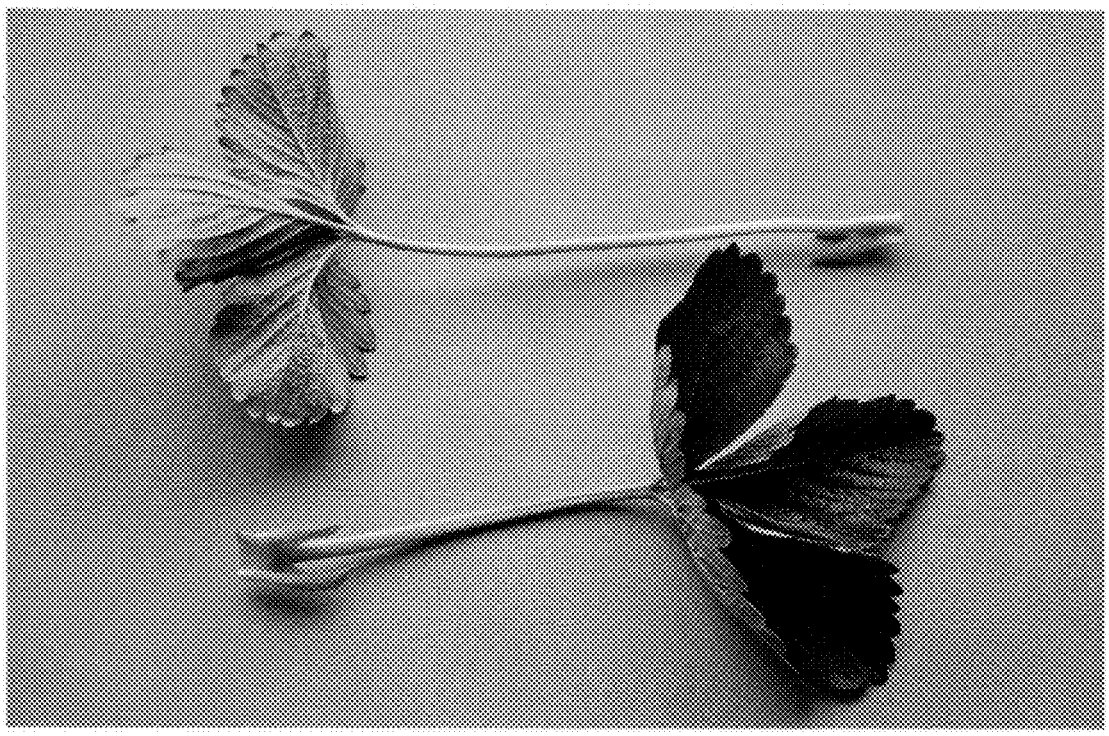
FIG. 2 shows upper and lower surfaces of the leaves of the plant with three leaflets.
Figure 3:
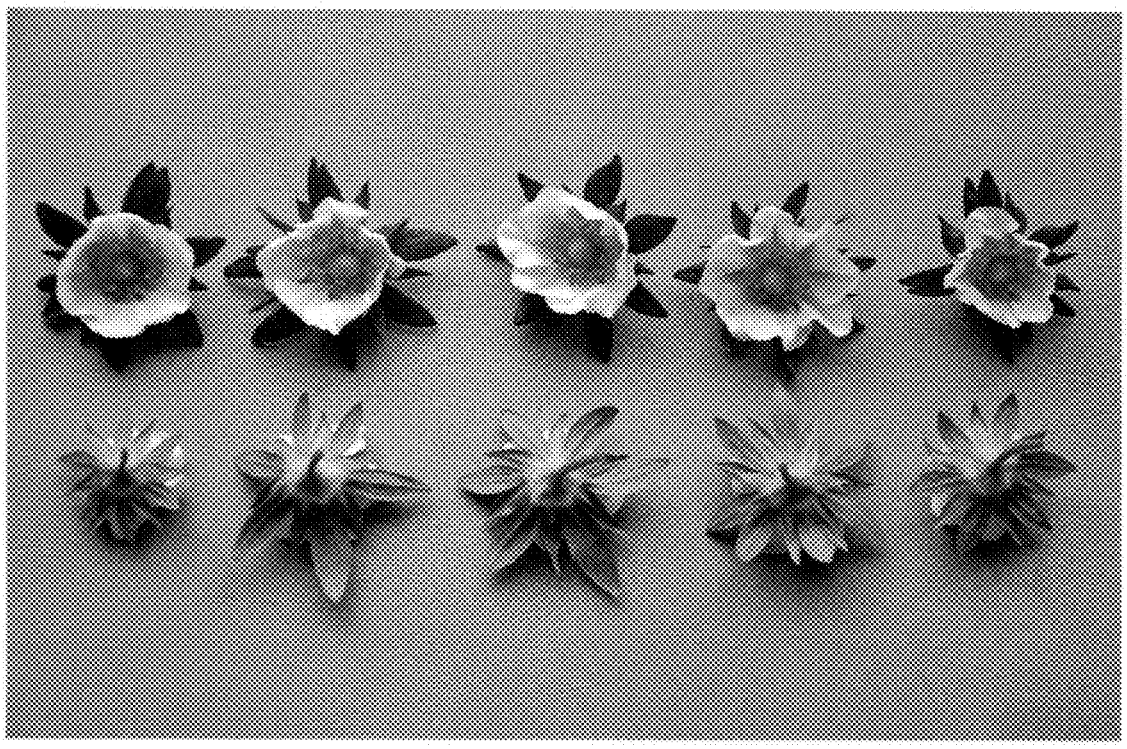
FIG. 3 shows both upper and lower surfaces of the flowers.
Figure 4:
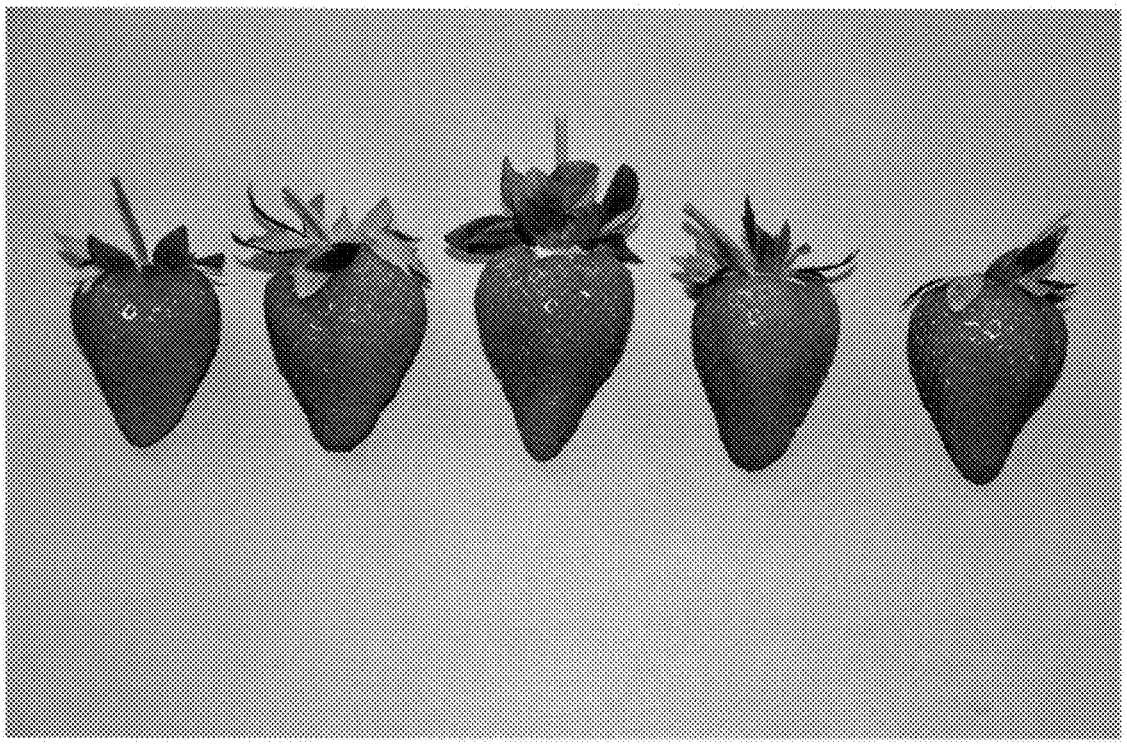
FIG. 4 shows the whole fruit.
Figure 5:
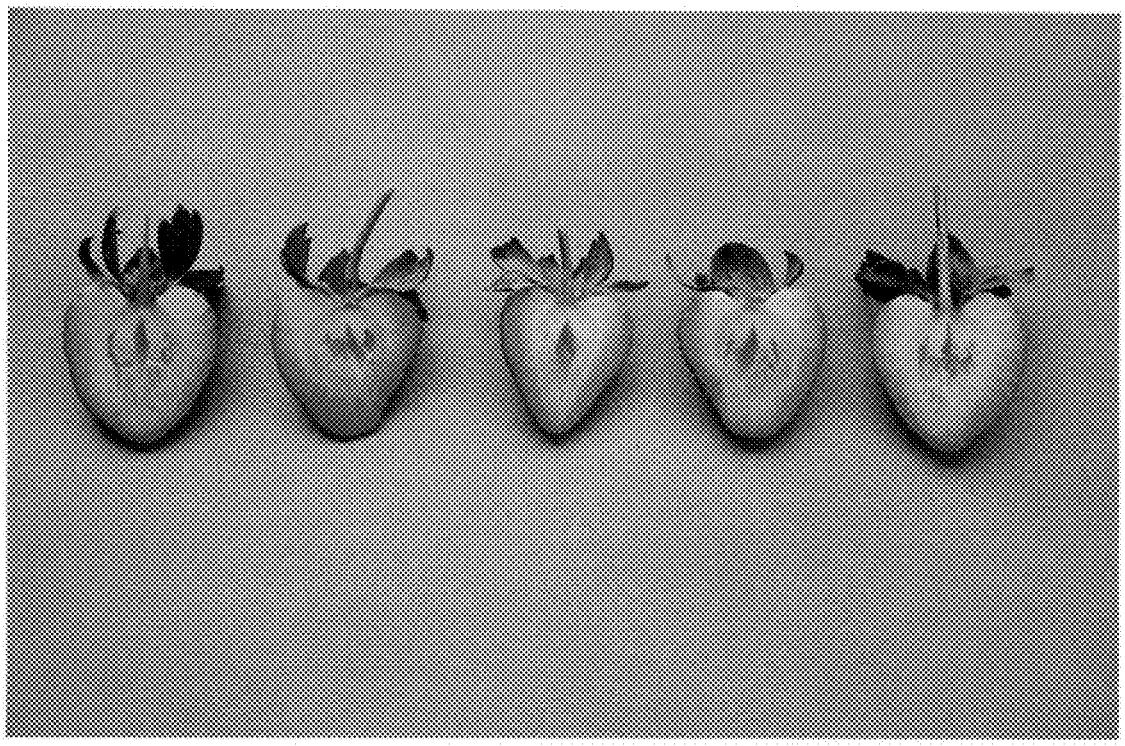
FIG. 5 shows the fruit in longitudinal cross-section.

The following detailed descriptions set forth the distinctive characteristics of 'DrisStrawTwentySix'. The data which define these characteristics is based on observations taken in Ventura County, Calif. from 2007 to 2011. This description is in accordance with UPOV terminology. Color designations, color descriptions, and other phenotypical descriptions may deviate from the stated values and descriptions depending upon variation in environmental, seasonal, climatic, and cultural conditions. 'DrisStrawTwentySix' has not been observed under all possible environmental conditions. The botanical description of 'DrisStrawTwentySix' was taken from six-month-old plants. Color terminology follows The Royal Horticultural Society Colour Chart (R.H.S.), London (2001 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION OF THE PLANT

Classification:
- *Species.*—*Fragaria×ananassa.*
- *Common name.*—Strawberry.
- *Denomination.*—'DrisStrawTwentySix'.

Parentage:
- *Female parent.*—The proprietary variety '18L33' (unpatented).
- *Male parent.*—The proprietary variety '193M68' (unpatented).

Plant:
- *Height.*—16.0 cm.
- *Diameter.*—33.3 cm.
- *Number of crowns/plant.*—3.

*Habit*.—Flat globose.
*Density of individual plant*.—Medium.
*Vigor* (*health and hardiness of plant*).—Medium.

Terminal leaflets:
*Size*.—Small. Length: 6.8 cm. Width: 5.9 cm. Length/width ratio: 1.2 (Longer than broad).
*Number of teeth/terminal leaflet*.—20.
*Shape of teeth*.—Obtuse-senate to crenate.
*Color*.—Upper surface: RHS 139A (Dark green). Lower surface: RHS 148C (Light yellow-green).
*Shape in cross section*.—Concave.
*Blistering*.—Medium.
*Glossiness*.—Strong.
*Number of leaflets*.—Three only.
*Shape*.—Oval.
*Base shape*.—Slightly oblique.
*Apex descriptor*.—Convex.
*Variegation*.—Absent.
*Margin*.—Senate.
*Margin profile*.—Flat (level with the leaflet blade).

Petiole:
*Length*.—11.6 cm.
*Diameter*.—3.43 mm.
*Pubescence*.—Medium.
*Pose of hairs*.—Outwards-horizontal.
*Color*.—RHS 144C (Medium yellow-green).

Petiolule:
*Length*.—4.97 mm.
*Diameter*.—1.49 mm.
*Bract frequency*.—0.
*Color*.—RHS 144C (Medium yellow-green).

Stipule:
*Length*.—3.1 cm.
*Width*.—8.73 mm.
*Pubescence*.—Medium.
*Anthocyanin coloration*.—Weak; RHS 51D (Light red).

Stolon:
*Number*.—Medium.
*Average number of daughter plants per plant*.—82.
*Anthocyanin coloration*.—Medium; RHS 35A (Medium orange-red).
*Thickness*.—Thick.
*Pubescence*.—Medium.

Inflorescence:
*Position relative to foliage*.—Above.
*Number of flowers*.—Many.
*Time of flowering* (*50% of plants at first flower*).—Very early.
*Flower size*.—Large.
*Flower diameter*.—33.56 mm.
*Petals*.—Shape: Orbicular. Apex: Rounded. Base: Concave-convex. Margin: Entire. Spacing: Overlapping. Length: 17.86 mm. Width: 17.00 mm. Length/width ratio: As long as broad; 1.1. Typical and observed petal number per flower: 6. Color (upper surface): RHS 155B (White).
*Calyx*.—Diameter: 46.93 mm. Diameter relative to corolla: Larger. Inner calyx diameter relative to outer: Smaller. Insertion of calyx: Level. Pose of calyx segments: Reflexed — upwards. Size of calyx in relation to fruit: Slightly larger. Adherence of calyx: Strong.
*Sepal*.—Shape: Elliptical. Apex: Convex. Margin: Entire. Length: 20.04 mm. Width: 7.28 mm. Typical and observed sepal number per flower: 13.
*Receptacle color*.—RHS 1B (Medium green-yellow).
*Stamen*.—Present. Anther color: RHS 15A (Medium yellow-orange).
*Pedicel*.—Attitude of hairs: Upwards.

Fruiting truss:
*Length*.—Long; 17.3 cm.
*Diameter at base of truss*.—2.51 mm.
*Number of berries per fruiting truss*.—3.
*Attitude at first picking*.—Prostrate.
*Color at base of truss*.—RHS 144A (Medium yellow-green).

Fruit:
*Relative fruit size*.—Large.
*Length*.—55.47 mm.
*Width*.—45.30 mm.
*Length/width ratio*.—1.2 (Longer than broad).
*Fruit hollow length*.—27.47 mm.
*Fruit hollow width*.—11.35 mm.
*Fruit hollow length/width ratio*.—2.4.
*Fruit hollow center* (*size*).—Large.
*Weight* (*per individual berry*).—30.0 g.
*Predominant fruit shape*.—Conical.
*Difference in shape between primary and secondary fruits*.—Slight.
*Evenness of fruit surface*.—Even or very slightly uneven.
*Fruit skin color*.—RHS 46A (Dark red).
*Evenness of fruit color*.—Even or very slightly uneven.
*Fruit glossiness*.—Medium.
*Achenes*.—Insertion of achenes: Below surface. Coloration (sunward side of berry): RHS 179B (Medium greyed-red). Coloration (shaded side of berry): RHS 153D (Medium yellow-green). Number per berry: 365. Weight (weight achenes divided by total # seed): 0.000548602. Width of band without achenes: Broad.
*Firmness of flesh*.—Medium.
*Color of flesh* (*excluding core*).—RHS 39B (Light red) and RHS 155A (White).
*Color of core*.—RHS 39B (Light red).
*Evenness of flesh color*.—Even.
*Distribution of flesh color*.—Marginal and central.
*Sweetness*.—Medium.
*Acidity*.—Medium.
*Texture when tasted*.—Medium.
*Type of bearing*.—Not everbearing — not remontant.
*Grams of fruit/plant*.—94.3 g.
*Harvest interval*.—December to July.
*Harvest maturity*.—Very early.

Disease, pest, and stress resistance:
*Botrytis fruit rot*.—Susceptible.
*Powdery mildew*.—Moderately susceptible.
*Verticillium wilt*.—Susceptible.
*Xanthomonas fragariae*.—Moderately susceptible.
*Aphis spp.* (*Aphids*).—Susceptible.
*Lygus hesperus* (*Lygus bug*).—Susceptible.
*High temperatures*.—Moderately susceptible.
*Wind*.—Moderately susceptible.
*High pH*.—Moderately resistant.
*High soil salt levels*.—Moderately resistant.

COMPARISON WITH PARENTAL AND COMMERCIAL VARIETIES

When 'DrisStrawTwentySix' is compared to the proprietary female parent '18L33' (unpatented), 'DrisStrawTwentySix' has earlier fruit production and smaller sized fruit than '18L33' and is less vigorous than '18L33'.

When 'DrisStrawTwentySix' is compared to the proprietary male parent '193M68' (unpatented), 'DrisStrawTwentySix' has earlier fruit production, larger fruit size with better flavor, and higher total yields than '193M68' and is less vigorous and has firmer fruit than '193M68'.

When 'DrisStrawTwentySix' is compared to the commercial variety 'Driscoll El Dorado' (U.S. Plant Pat. No. 16,238), 'DrisStrawTwentySix' has a medium density, flat globose habit that is not everbearing, with strongly glossy leaves and a slightly oblique terminal leaflet base, while 'Driscoll El Dorado' has a dense, globose habit that is partially everbearing, with medium glossy leaves and a rounded terminal leaflet base. Additionally, 'DrisStrawTwentySix' has thick stolons and a broad band without achenes, while 'Driscoll El Dorado' has thin stolons and a narrow to medium band without achenes.

When 'DrisStrawTwentySix' is compared to the commercial variety 'DrisStrawEight' (U.S. Plant Pat. No. 20,735), 'DrisStrawTwentySix' has a flat globose habit that is not everbearing, with strongly glossy leaves, a flat terminal leaflet margin and an oval terminal leaflet shape, while 'DrisStrawEight' has a globose habit that is partially everbearing, with weakly glossy leaves, a revolute terminal leaflet margin and an orbicular terminal leaflet shape. Additionally, 'DrisStrawTwentySix' has thick stolons and three berries per fruiting truss, while 'DrisStrawEight' has thin stolons and one berry per fruiting truss.

We claim:

1. A new and distinct variety of strawberry plant named 'DrisStrawTwentySix' as described and shown herein.

* * * * *